United States Patent [19]

Ilvespaa

[11] 4,006,184
[45] Feb. 1, 1977

[54] 1- OR 2-[2-HYDROXY-3-AMINO-PROPOXY]-9,10-DIHYDRO-9,10-ETHANO-ANTHRACENES AND THEIR SALTS

[75] Inventor: Atso Ilvespaa, Allschwil, Switzerland

[73] Assignee: Ciba-Geigy Corporation, Ardsley, N.Y.

[22] Filed: Apr. 4, 1974

[21] Appl. No.: 457,741

[30] Foreign Application Priority Data

Apr. 17, 1973 Switzerland .................. 5500/73

[52] U.S. Cl. ............... 260/570.7; 260/243 B; 260/247.7 R; 260/268 TR; 260/293.9; 260/326.5 M; 260/343.7; 260/348 R; 260/465 E; 260/471 C; 260/501.12; 260/501.18; 260/501.19; 260/566 F; 260/567.5; 260/599; 424/248.58; 424/246; 424/250; 424/267; 424/274; 424/280; 424/304; 424/316; 424/330

[51] Int. Cl.² ................ C07C 93/06

[58] Field of Search ...... 260/570.7, 501.12, 501.15

[56] References Cited

UNITED STATES PATENTS

| | | | |
|---|---|---|---|
| 3,394,171 | 7/1968 | Thompson | 260/570.7 X |
| 3,415,873 | 12/1968 | Stevens | 260/570.7 X |
| 3,422,106 | 1/1969 | Boissier et al. | 260/570.7 X |
| 3,634,507 | 1/1972 | Boissier et al. | 260/570.7 X |
| 3,732,308 | 5/1973 | Lauria et al. | 260/570.7 |

Primary Examiner—Robert V. Hines
Attorney, Agent, or Firm—Joseph G. Kolodny; John J. Maitner; Theodore O. Groeger

[57] ABSTRACT

Amines of the formula Ia

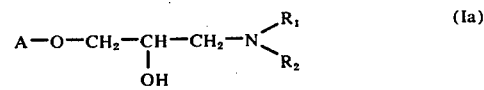

(Ia)

wherein A is a 1- or 2-[9,10-dihydro-9,10-ethono(or etheno)anthryl] radical, especially of the formula Ib

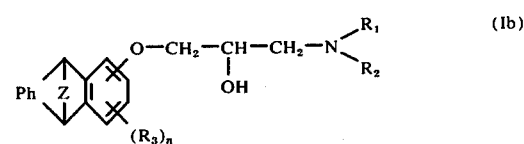

(Ib)

wherein Ph denotes an optionally substituted o-phenylene radical, Z represents an optionally lower-alkylated ethylene or ethenylene radical, $R_3$ denotes lower alkyl radicals, lower alkoxy radicals, hydroxyl groups, nitro groups, amino groups, trifluoromethyl groups, nitrile or halogen atoms or above all hydrogen and $n$ represents the numbers 1, 2 or 3, $R_1$ denotes hydrogen or lower alkyl and $R_2$ is hydrogen, lower alkyl, aryl-lower alkyl or optionally functionally modified carboxy-lower alkyl, or $R_1$ and $R_2$ together represent a divalent hydrocarbon radical of aliphatic character which can optionally be interrupted by hetero-atoms and/or be substituted, which are valuable excitations inhibitors and nacosic-boosting compounds.

7 Claims, No Drawings

1- OR 2-[2-HYDROXY-3-AMINO-PROPOXY]-9,10-DIHYDRO-9,10-ETHANO-ANTHRACENES AND THEIR SALTS

The invention relates to new amines of the formula Ia

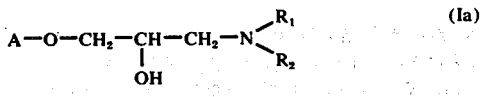

wherein A is a 1- or 2-[9,10-dihydro-9,10-ethano(or etheno)-anthryl] radical, especially of the formula Ib

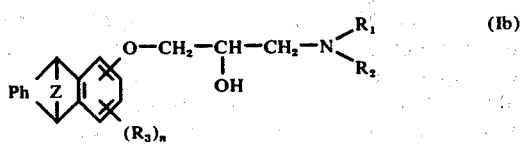

wherein Ph denotes an optionally substituted o-phenylene radical, Z represents an optionally lower-alkylated ethylene or ethenylene radical, $R_3$ denotes lower alkyl radicals, lower alkoxy radicals, hydroxyl groups, nitro groups, amino groups, trifluoromethyl groups, nitrile or halogen atoms or above all denotes hydrogen and n represents the numbers 1, 2 or 3, $R_1$ denotes hydrogen or lower alkyl and $R_2$ is hydrogen, lower alkyl, aryl-lower alkyl or optionally functionally modified carboxy-lower alkyl or $R_1$ and $R_2$ together represent a divalent hydrocarbon radical of aliphatic character which can optionally be interrupted by hetero-atoms and/or can be substituted, and processes for their preparation.

Optionally lower-alkylated ethylene or ethenylene radicals Z are ethylene or ethenylene radicals substituted by the lower alkyl radicals of 1–7 C atoms listed below, or above all unsubstituted ethylene or ethenylene.

The o-phenylene radical Ph can be substituted by lower alkyl radicals, lower alkoxy radicals, hydroxyl groups, nitro groups, amino groups, trifluoromethyl groups, nitrile or above all halogen atoms, for example those indicated below, but is preferably unsubstituted.

Lower alkyl radicals are above all radicals with up to 7 C atoms, such as methyl, ethyl, iso- or n-propyl radicals or straight or branched butyl, pentyl, hexyl or heptyl radicals bonded in any desired position. Lower alkoxy radicals are in particular those radicals which contain the lower alkyl radical mentioned, above all methoxy and ethoxy radicals.

Halogen atoms are, for example, fluorine, bromine or, especially, chlorine atoms.

Lower alkyl $R_2$ preferably has up to 7 C atoms, above all up to 4 C atoms, and is unbranched or branched, especially branched at the $\alpha$-C atom, and is, for example, ethyl, propyl, butyl or especially methyl, sec.-butyl, tert.-butyl or isopropyl.

Aryl-lower alkyl $R_2$ preferably has up to 12 C atoms, above all up to 10 C atoms, and is unbranched, or preferably branched, in the lower alkyl part and in particular branched at the $\alpha$-C atom of the lower alkyl part. The aryl part represents in particular a phenyl radical which is optionally polysubstituted or especially mono-substituted by lower alkyl, such as that mentioned above, lower alkoxy, such as that mentioned above, halogen, such as that mentioned above, or trifluoromethyl, but is preferably unsubstituted. Examples of aryl-lower alkyl $R_2$ are 1-methyl-3-phenyl-propyl and especially 1-methyl-2-phenyl-ethyl.

Optionally functionally modified carboxy-lower alkyl preferably has up to 7 C atoms, above all up to 4 C atoms, in the lower alkyl part, and is unbranched or preferably branched, especially branched at the $\alpha$-C atom. Optionally functionally modified carboxy-lower alkyl is thus carboxymethyl, 1-carboxy-1-methyl-ethyl, 3-carboxy-1-methyl-propyl or especially 2-carboxyethyl or above all 2-carboxy-1-methylethyl, these being preferably functionally modified at the carboxyl group. The optionally functionally modified carboxyl group is, for example, free, esterified or amidised carboxyl, or nitrile.

Esterified carboxyl is, for example, carboxyl esterified with an aliphatic alcohol. Aliphatic alcohols are those in which the hydroxyl group is bonded to a C atom which is not a member of an aromatic system. Examples of suitable aliphatic alcohols are cycloalkanols, such as those with 3–7, especially 5–7, ring members, for example, cyclopropanol, cyclopentanol, cyclohexanol and cycloheptanol, cycloalkyllower alkanols, which contain, for example, the above cycloalkyl parts, such as cyclopentyl-methanol, cyclohexylmethanol, 2-cyclohexyl-ethanol and cycloheptyl-methanol, phenyl-lower alkanols, such as 2-phenylethanol and benzyl alcohol, wherein phenyl radicals can also be substituted by halogen, lower alkyl and/or lower alkoxy, such as those mentioned above, and especially lower alkanols, such as n-propanol, iso-propanol, straight-chain or branched butanol, pentanol, hexanol or heptanol, and especially methanol or ethanol. Thus, esterified carboxyl is above all methoxycarbonyl or ethoxycarbonyl.

Amidised carboxyl is substituted or unsubstituted carbamoyl. Substituted carbamoyl has, for example, the formula $-CO-NR_5R_6$, wherein $R_5$ is hydrogen or lower alkyl, $R_6$ is lower alkyl or $R_5$ $R_6$ together are lower alkylene, oxalower alkylene, thia-lower alkylene or aza-lower alkylene. Lower alkyl is especially that mentioned above.

Lower alkylene is branched or especially straight-chain lower alkylene with, especially, 2–7 above all 4–6, C atoms in the alkylene chain and, together with the N atom which bonds the lower alkylene, especially represents pyrrolidino or piperidino.

Oxa-lower alkylene is branched or, especially, straight-chain oxa-lower alkylene with, especially, 4 or 5 C atoms in the oxaalkylene chain and, together with the N atom which bonds the oxa-lower alkylene, especially represents morpholino.

Thia-lower alkylene is branched or especially straight-chain thia-lower alkylene with, especially, 4 or 5 C atoms in the thiaalkylene chain and, together with the N atom which bonds the thia-lower alkylene, especially represents thiomorpholino or 2,6-dimethylthiomorpholino.

Aza-lower alkylene is branched or straight-chain aza-lower alkylene with, especially, 2–6, above all 4–6, C atoms in the azaalkylene chain and, together with the N-atom which bonds the aza-lower alkylene, especially represents piperazino, N'-lower alkylpiperazino, such as N'-methylpiperazino or N'-($\beta$-hydroxyethyl)-piperazino.

Divalent hydrocarbon radicals of aliphatic character which are represented by $R_1$ and $R_2$ together, and which can optionally be interrupted by hetero-atoms and/or can be substituted, are preferably lower alkylene radicals which can be straight-chain or branched and above all possess 4–6 chain carbon atoms if the carbon chain is uninterrupted or 4 or 5 chain carbon atoms if the carbon chain is interrupted by hetero-atoms. Possible hetero-atoms are especially oxygen, sulphur and nitrogen. Examples of such radicals are butylene-(1,4), pentylene-(1,5), hexylene-(1,5), hexylene-(2,5), hexylene-(1,6), heptylene-(1,6), 3-oxapentylene-(1,5), 3-oxo-hexylene(1,6), 3-thia-pentylene-(1,5), 2,4-dimethyl-3-thia-pentylene-(1,5), 3-aza-pentylene-(1,5), 3-lower alkyl-3-aza-pentylene-(1,5), such as 3-methyl-3-aza-pentylene-(1,5), 3-azahexylene-(1,6), 3-(β-hydroxyethyl)-3-aza-pentylene-(1,5) or 3-[2-oxo-1-imidazolidinyl]-pentylene-(1,5).

The new compounds possess valuable pharmacological properties. Thus, the new compounds have a central-depressant action, as can be shown in determining the pargylinreserpine antagonism in mice, at does of 1–10 ml/kg administered intraperitoneally.

The new compounds furthermore have a narcosis-boosting action; for example, the duration of action of the short-term narcotic 2-methoxy-4-allyl-phenoxy-acetic acid N,N-diethylamide is prolonged significantly, as can be shown at doses of 40 mg/kg administered to mice.

The new compounds therefore are useful as exicitation inhibitors. However, they can also be used as valuable intermediate products for the manufacture of other useful substances, especially pharmaceutically active compounds.

Particularly valuable compounds are those of the formula II

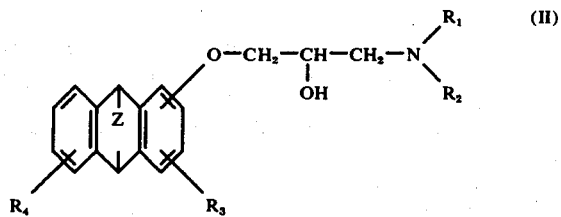

wherein $R_4$ and $R_3$ independently of one another have the meaning mentioned above for $R_3$ and Z, $R_1$ and $R_2$ have the abovementioned meaning.

Compounds to be singled out are above all those of the formula II, herein Z and $R_1$ have the abovementioned meaning, $R_4$ and $R_3$ independently of one another denote methoxy groups or chlorine atoms or, especially, hydrogen atoms and $R_2$ denotes hydrogen or a —C($R_7$)($R_8$)($R_9$) group, wherein $R_7$ and $R_8$ independently of one another denote hydrogen or lower alkyl, for example methyl, ethyl, propyl, isopropyl or butyl and $R_9$ represents hydrogen, aryl or arylalkyl, wherein the aryl part of the molecule can optionally be substituted by lower alkyl, lower alkoxy, halogen and/or trifluoromethyl, or represents lower alkyl, or lower alkyl which is optionally substituted by the carboxyl group, by lower alkoxycarbonyl, carbamoyl, N-lower alkylcarbamoyl, N,N-di-lower alkylcarbamoyl, N,N-lower alkylenecarbamoyl, N,N-oxa-lower alkylenecarbamoyl, N,N-thia-lower alkylenecarbamoyl, N,N-aza-lower alkylenecarbamoyl or nitrile.

Amines to be particularly singled out are those of the formula III

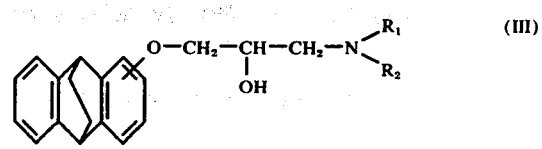

wherein $R_1$ and $R_2$ have the abovementioned meaning and the 3-amino-2-hydroxypropoxy side chain is in the 1- or 2-position of the anthracene skeleton.

Amines to be singled out very particularly are those of the formula III, wherein $R_1$ represents hydrogen or lower alkyl, such as methyl, and $R_2$ denotes hydrogen or a —CH($R_8$)($R_9$) group, wherein $R_8$ represents hydrogen or methyl and $R_9$ represents hydrogen, phenyl or phenylalkyl, wherein the phenyl part of the molecule can optionally be substituted by lower alkyl, lower alkoxy, halogen and/or trifluoromethyl, or represents lower alkyl or lower alkyl which is optionally substituted by carboxyl, methoxycarbonyl, ethoxycarbonyl, carbamoyl, N-methylcarbamoyl, N,N-dimethylcarbamoyl, pyrrolidinocarbonyl, piperidinocarbonyl, morpholinocarbonyl, thiomorpholinocarbonyl, piperazinocarbonyl, N'-methylpiperazinocarbonyl or nitrile, and the 3-amino-2-hydroxypropoxy side chain is in the 1- or 2-position of the anthracene skeleton.

Amongst the amines singled out above, there should especially be mentioned amines of the formula III, wherein $R_1$ represents hydrogen or methyl and $R_2$ denotes hydrogen, lower alkyl with 1 to 7 C atoms or a —CH($CH_3$)($R_9$) group, and $R_9$ represents phenyl or benzyl or represents a —$CH_2$—$R_{10}$ radical, wherein $R_{10}$ represents carboxyl, methoxycarbonyl, ethoxycarbonyl, carbamoyl, N-methylcarbamoyl, N,N-dimethylcarbamoyl, pyrrolidinocarbonyl, piperidinocarbonyl, morpholinocarbonyl, thiomorpholinocarbonyl, piperazinocarbonyl, N'-methylpiperazinocarbonyl or nitrile, and the 3-amino-2-hydroxypropoxy side chain is in the 1- or 2-position of the anthracene skeleton.

Amongst the amines of the formula III, there should be mentioned very especially those wherein $R_1$ denotes hydrogen or methyl and $R_2$ represents hydrogen, lower alkyl with 1 to 7 C atoms, above all with 3-4 C atoms, or a —CH($CH_3$)$CH_2$—$R_{10}$ group, wherein $R_{10}$ represents carboxyl, methoxycarbonyl, carbamoyl or nitrile and the 3-amino-2-hydroxypropoxy side chain is in the 1- or 2-position of the anthracene skeleton.

Amines of very particular importance are those of the formula III wherein $R_1$ represents hydrogen or lower alkyl, such as methyl, $R_2$ represents hydrogen or lower alkyl, such as methyl, ethyl, isopropyl or tert. butyl and the 3-amino-2-hydropropoxy side chain is in the 1- or 2-position of the anthracene skeleton, and very particularly the compounds mentioned in the examples.

The new compounds are obtained according to methods which are in themselves known.

Thus it is possible, for example, to react a compound $$A-O-CH_2-CH(X_1)-CH_2-Z_1 \tag{IV}$$

with a compound $$X_2-R^{**} \tag{V}$$

wherein one of the radicals $Z_1$ and $Z_2$ represents the $-NH-R^x$ radical and the other denotes a reactive esterified hydroxyl group, one of the radicals $R^x$ and $R^{xx}$ represents $R_1$, the other represents $R_2$, with A, $R_1$ and $R_2$ having the above meaning, and $X_1$ is hydroxyl, or wherein $Z_1$ together with $X_1$ forms an epoxy group and $Z_2$ represents $NH-R^x$, wherein $R^x$ represents $R_1$ or $R_2$. $Z_1$ must however not denote $-NH_2$.

A reactive esterified hydroxyl group is especially a hydroxyl group esterified by a strong inorganic or organic acid, above all a hydrogen halide acid, such as hydrochloric acid, hydrobromic acid or hydriodic acid, or sulphuric acid, or by a strong organic sulphonic acid, such as a strong aromatic sulphonic acid, for example benzenesulphonic acid, 4-bromobenzenesulphonic acid or 4-toluenesulphonic acid. Thus $Z_1$ or $Z_2$ especially represents chlorine or bromine.

This reaction is carried out in the usual manner. If a reactive ester is used as the starting material, the reaction is preferably carried out in the presence of a basic condensation agent and/or with an excess of amine. Suitable basic condensation agents are, for example, alkali metal hydroxides, such as sodium hydroxide or potassium hydroxide, alkali metal carbonates, such as potassium carbonate, and alkali metal alcoholates, such as sodium methylate, potassium ethylate and potassium tertiary butylate.

It is also possible to react a compound A-OH (VI) with a compound $Z_3-CH_2-CH(X_1)-CH_2-N(R_1)(R_2)$ (VII), wherein A, $R_1$ and $R_2$ have the above meanings, $Z_3$ is a reactive esterified hydroxyl group and $X_1$ is hydroxyl or $Z_3$ and $X_1$ together are an epoxy group or, if $R_1$ or $R_2$ represents hydrogen, $Z_3$ together with the hydrogen of the amino group can also be a direct bond.

A reactive esterified hydroxyl group is especially one of those mentioned above.

This reaction is carried out in the usual manner. If reactive esters are used as the starting material, the compound of the formula VI can be used preferably in the form of its metal phenolate, such as alkali metal phenolate, for example sodium phenolate, or the reaction is carried out in the presence of an acid-binding agent, especially of a condensation agent which can form a salt with the compound of the formula VI, such as an alkali metal alcoholate or an alkali metal carbonate, such as potassium carbonate.

Furthermore it is possible, in a compound of the formula Ia, wherein A, $R_1$ and $R_2$ have the above meanings and which possess a removable radical on the nitrogen atom of the amino group and/or on the hydroxyl group, to remove this radical or these radicals. If such a compound carries a removable radical on the nitrogen atom of the amino group or both on the nitrogen atom of the amino group and on the hydroxyl group, $R_1$ in the resulting compounds is hydrogen.

Such removable radicals are especially radicals which can be removed by solvolysis or reduction.

Radicals which can be removed by solvolysis are especially radicals which can be removed by hydrolysis or ammonolysis.

Radicals which can be removed by hydrolysis are, for example, acyl radicals, such as optionally functionally modified carboxyl groups, for example oxycarbonyl radicals, such as alkoxycarbonyl radicals, for example the tert.-butoxycarbonyl radical or the ethoxycarbonyl radical, aralkoxycarbonyl radicals, such as phenyl-lower alkoxycarbonyl radicals, for example a carbobenzoxy radical, halogenocarbonyl radicals, for example the chlorocarbonyl radical, and also arylsulphonyl radicals, such as toluenesulphonyl or bromobenzenesulphonyl radicals, and optionally halogenated, such as fluorinated, lower alkanoyl radicals, for example the formyl, acetyl or trifluoroacetyl radical, or aroyl radicals which are optionally substituted like the radical Ph, for example the benzoyl radical, or nitrile groups or silyl radicals, such as the trimethylsilyl radical.

Possible radicals on the hydroxyl group which can be split off by hydrolysis are, amongst those mentioned, especially oxycarbonyl radicals and lower alkanoyl radicals or benzoyl radicals.

Compounds with radicals which can be removed by hydrolysis are, for example, also compounds of the formula VIII

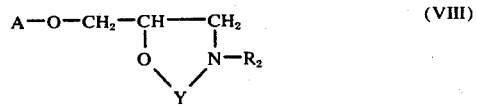

wherein A and $R_2$ have the above meanings and Y represents a carbonyl or thiocarbonyl radical or a divalent radical of an aldehyde or ketone.

Ketones are, for example, di-lower alkyl ketones, such as methyl ethyl ketone or acetone, or lower alkyl aryl ketones, such as phenyl methyl ketone, whilst aldehydes are, for example, lower alkanals, such as those with especially up to 7 C atoms, such as acetaldehyde and above all formaldehyde, or aryl-lower alkanals, such as phenyl-lower alkanals, for example benzaldehyde or 2-, 3- or 4-pyridinaldehyde.

The hydrolysis is carried out in the usual manner, for example in the presence of hydrolysing agents, for example in the presence of acid agents, such as, for example, mineral acids, such as sulphuric acid or hydrogen halide acid, or in the presence of basic agents, for example alkali metal hydroxides, such as sodium hydroxide. Oxycarbonyl radicals, arylsulphonyl radicals and nitrile groups can advantageously be removed by acid agents, such as by a hydrogen halide acid, especially hydrobromic acid. Furthermore, for example, a tert.-butoxycarbonyl radical can be removed in the presence of small amounts of water or under anhydrous conditions by treatment with a suitable acid, such as trifluoroacetic acid. In the hydrolysis of compounds of the formula V, especially, acid agents are suitably used.

Radicals which can be removed by reduction are, for example, α-arylalkyl radicals, such as benzyl radicals, or α-aralkoxycarbonyl radicals, such as benzyloxycarbonyl radicals, which can be removed in the usual manner by hydrogenolysis, especially by catalytically activated hydrogen, such as by hydrogen in the presence of a hydrogenation catalyst, for example platinum, palladium or Raney nickel. Further radicals which can be removed by reduction are, for example, 2-halogenoalkoxycarbonyl radicals, such as the 2,2,2-trichloroethoxy-carbonyl radical or the 2-iodoethoxy-carbonyl or 2,2,2-tribromoethoxy-carbonyl radical, which can be removed in the usual manner, especially by metallic reduction (so-called nascent hydrogen). Nascent hydrogen can be obtained by the action of metal or metal alloys, such as amalgams, on hydrogen donors, such as carboxylic acids, alcohols or water, and in particular zinc or zinc alloys together with acetic acid can be used. The reduction of 2-halogeno-alkoxycarbonyl radicals can furthermore be effected by chromium-(II) compounds, such as chromium-(II) chloride or chromium-(II) acetate. A radical which can be removed by reduction can also be an arylsulphonyl group, such as the toluenesulphonyl group, which can be removed in the usual manner by reduction with nascent hydrogen, for example by means of an alkali metal, such as lithium or sodium, in liquid ammonia, and can in particular be removed from a N atom. In carrying out the reduction, it is necessary to ensure that other reducible groups are not attacked.

It is furthermore possible to reduce a Schiff's base A—O—CH$_2$—CH(OH)—CH=N—R$_2$ (IX) or A—O—CH$_2$—CH(OH)—CH$_2$—N=R$_2'$ (X) or a ring tautomer corresponding to the formula X, of the formula Xa

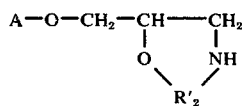

(Xa)

wherein A and R$_2$ have the above meaning and R$_2'$H is identical to R$_2$, it also being possible for compounds of the formulae X and Xa to be present alongside one another.

This reduction is carried out in the usual manner, for example by means of a di-light metal hydride, such as sodium borohydride, with a hydride, such as borane, with formic acid or by catalytic hydrogenation, such as with hydrogen in the presence of Raney nickel. Care must be taken in carrying out the reduction that other reducible groups are not attacked.

Within the scope of the end products it is possible in the usual manner to modify, introduce or remove substituents in resulting compounds, or to convert resulting compounds into other end products in the usual manner.

Thus it is possible, in resulting compounds which contain a C—C double bond, to convert the C—C double bond in the usual manner into a C—C single bond by catalytic hydrogenation, such as by hydrogen in the presence of a hydrogenation catalyst, for example platinum, palladium or nickel such as Raney nickel.

In the abovementioned reductions it is at times necessary to ensure that further reducible groups are not attacked. Thus, especially in the case of the reduction with Raney nickel and hydrogen, it is necessary to ensure that halogen atoms which may be present bonded to aromatic rings are not replaced by hydrogen. If necessary, the hydrogen absorption must be followed volumetrically during catalytic hydrogenations and the hydrogenation discontinued after the calculated amount has been absorbed.

In resulting compounds, the phenyl nucleus can be halogenated. This can be done in the usual manner, especially at room temperature or with cooling and in the presence of a catalyst, such as iron, iodine, iron-III chloride, aluminium chloride or the corresponding bromides.

In resulting compounds in which R$_1$ and/or R$_2$ denote hydrogen, the hydrogen can be replaced by the radicals R$_1$ or R$_2$ by reaction with compounds of the formula Z$_4$—R$_1$ or Z$_4$—R$_2$, wherein Z$_4$ represents a reactive esterified hydroxyl group, This reaction is carried out in the usual manner. If a reactive ester is used as the starting material, the reaction is preferably carried out in the presence of a basic condensation agent and/or with an excess of amine. Suitable basic condensation agents are, for example, alkali metal hydroxides, such as sodium hydroxide or potassium hydroxide, alkali metal carbonates, such as potassium carbonate, and alkali metal alcoholates, such as sodium methylate, potassium ethylate and potassium tertiary butylate.

In resulting compounds, functionally modified carboxyl groups forming a constituents of R$_2$ can be hydrolysed in the usual manner to give free carboxyl groups, preferably in the presence of a strong base, such as a strong organic or above all inorganic base, preferably a metal base, for example an alkaline earth metal carbonate or alkali metal carbonate or above all an alkaline earth metal hydroxide or alkali metal hydroxide, for example calcium hydroxide, sodium hydroxide or potassium hydroxide, or a strong acid, for example a strong mineral acid, especially hydrogen halide acid, for example hydrochloric acid, or sulphuric acid. If desired, oxidising agents, such as nitrous acid, can be added when hydrolysing the carbamoyl group.

The nitrile group, as a constituent of R$_2$, can also be hydrolysed to the carbamoyl group in the usual manner, for example as described above for the hydrolysis to the free carboxyl group. Equally, the carbamoyl group can also be converted to the nitrile group by dehydration in the usual manner, for example by heating and/or by the action of dehydrating agents.

Free carboxyl groups as a constituent of R$_2$ can be esterified in the usual manner, for example by reaction with a corresponding alcohol, advantageously in the presence of an acid, such as a mineral acid, for example sulphuric acid or hydrochloric acid, or in the presence of a water-binding agent, such as dicyclohexylcarbodiimide, or by reaction with a corresponding diazo compound, for example a diazoalkane. The esterification can also be effected by reaction of a salt, preferably of an alkali metal salt, of the acid with a reactively esterified alcohol, for example a halide, such as the chloride, of the corresponding alcohol.

Free carboxyl groups can also be converted into amidised carboxyl groups in the usual manner, for example by reaction with ammonia or a primary or secondary amine and, if necessary, dehydration of the ammonium salt formed as an intermediate.

Free carboxyl groups can, for example, also be converted into acid halide or acid anhydride groups in the usual manner, for example by reaction with halides of phosphorus or sulphur, such as thionyl chloride, phosphorus pentachloride or phosphorus tribromide, or with acid halides, such as chloroformic acid esters or oxalyl chloride. These acid halide or acid anhydride groups can be converted into esters or amides by reaction respectively with an alcohol or with ammonia or with a primary or secondary amine, if desired in the presence of acid-binding agents, such as organic or inorganic bases. Resulting nitriles can also be converted analogously, by reaction with an alcohol into the corresponding imino-ethers, which can be hydrolysed in the usual manner to the corresponding esters.

In resulting compounds in which carboxyl is a constituent of R$_2$, carbon dioxide can furthermore be split off. The splitting off of carbon dioxide (decarboxylation) can be effected in the usual manner, for example by heating, optionally in the presence of an inert solvent, for example diphenyl ether or quinoline. However, it is also possible to start from resulting compounds in which an esterified carboxyl group is a constituent of $R_2$, and to heat these compounds in the presence of a hydrolysis catalyst, such as an acid or basic agent, whereby the corresponding free acid or a salt thereof is obtained as an intermediate and then undergoes decarboxylation.

The reactions mentioned can optionally be carried out simultaneously or successively and in any desired sequence.

The reactions mentioned are carried out in the usual manner in the presence or absence of diluents, condensation agents and/or catalytic agents, at lowered, ordinary or raised temperature and, if appropriate, in a closed vessel.

Depending on the process conditions and starting materials, the end products are obtained in the free form or in the form of their acid addition salts which is also encompassed by the invention. Thus, for example, basic, neutral or mixed salts and if relevant also hemihydrates, monohydrates, sesquihydrates or polyhydrates thereof, can be obtained. The acid addition salts of the new compounds can be converted into the free compound in a manner which is in itself known, for example by means of basic agents, such as alkalis or ion exchangers. On the other hand, the resulting free bases can form salts with organic or inorganic acids. Acids used to prepare acid addition salts are especially those suitable for forming therapeutically usable salts. As examples of such acids there may be mentioned: Hydrogen halide acids, sulphuric acid, phosphoric acids, nitric acid, fumaric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid or pyruvic acid, benzoic acid, anthranilic acid, p-hydroxybenzoic acid, salicylic acid or embonic acid, methanesulphonic acid, ethanesulphonic acid, hydroxyethanesulphonic acid, ethylenesulphonic acid, halogenohenzenesulphonic acids, toluenesulphonic acid, cyclohexylaminesulphonic acid or sulphanilic acid.

These or other salts of the new compounds such as, for example, the picrates, can also be used for purifying the free bases obtained, by converting the free bases into salts, isolating these and again liberating the bases from the salts. Because of the close relationships between the new compounds in the free form and in the form of their salts, the free compounds are to be understood, in the preceding and following text, where appropriate also to include the corresponding salts, in general sense and intended use.

The invention also relates to those embodiments of the process according to which a compound obtainable as an intermediate product at any stage of the process is used as the starting product and the missing process steps are carried out, or the process is discontinued at any state, or in which a starting material is formed under the reaction conditions or in which a reactant is present in the form of its salts, if appropriate.

Thus it is possible to react an aldehyde A—O—CH$_2$—CH(OH)—CHO (XI) with an amine of the formula H$_2$N—R$_2$, wherein a and R$_2$ have the above meaning, in the presence of a suitable reducing agent, such as one of those mentioned above. This gives a compound of the formula IX as an intermediate product, which is then reduced in accordance with the invention.

It is furthermore possible suitably to react an amine of the formula IV, wherein $Z_1$ represents a free amino group, with an aldehyde or ketone of the formula O=R$_2$', wherein R$_2$' has the above meaning, in the presence of a suitable reducing agent, such as one of those mentioned above. This give, as an intermediate product, a compound of the formula X or Xa, which is then reduced in accordance with the invention.

Depending on the choice of the starting materials and procedures, the new compounds can be in the form of optical antipodes or racemates or, it they contain at least two asymmetrical carbon atoms, also in the form of isomer mixtures (racemate mixtures).

Resulting isomer mixtures (racemate mixtures) can be separated into the two stereoisomeric (diastereomeric) pure racemates on the basis of the physico-chemical differences of the constituents, in a known manner, for example by chromatography and/or fractional crystallisation.

Resulting racemates can be resolved according to known methods, for example by recrystallisation from an optically active solvent, with the aid of micro-organisms or by reaction with an optically active acid which forms salts with the racemic compound, and separation of the salts obtained in this manner, for example on the basis of their different solubilities, into the diastereomers, from which the antipodes can be liberated by the action of suitable agents. Examples of particularly customary optically active acids are the D- and L-forms of tartaric acid, di-o-toluyltartaric acid, malic acid, mandelic acid, camphorsulphonic acid or quinic acid. Advantageously, the more active of the two antipodes is isolated.

Suitably, those starting materials are used for carrying out the reactions according to the invention as lead to the groups of end products particularly mentioned initially, and particularly to the end products which have been especially described or singled out.

The starting materials are known or can, if they are new, be obtained according to methods which are in themselves known.

The compounds of the formula VI required as starting materials are obtained, for example, by 1,4-cycloaddition of ethylene or acetylene to the hydroxyanthracenes corresponding to the formula VI, as is shown in Example 1.

Starting materials of the formula IV can be obtained by reaction of the corresponding compounds of the formula VI with epichlorohydrin, for example as in Example 1.

Starting materials of the formula IV, wherein $Z_1$ represents a free amino group, can be obtained from the corresponding epoxides with ammonia, analogously to Examples 1 and 2.

The compounds of the formula VII mentioned as starting materials can be prepared by reaction of epichlorohydrin with amines HN(R$_1$)(R$_2$).

The starting materials of the formula XI are obtained, for example, by reaction of compounds A-OH with the diethylacetal of 2,3-oxidopropanal (compare U.S. Pat No. 2,631,163) and saponification of A—O—CH$_2$CH(OH)—CH(OC$_2$H$_5$)$_2$ thus formed, to give the aldehyde of the formula XI.

The new compounds can be used as medicaments, for example in the form of pharmaceutical preparations, in which they or their salts are present mixed with a pharmaceutical, organic or inorganic, solid or liquid excipient which is suitable, for example, for enteral, for example oral or parenteral, administration. Possible materials for forming the excipient are those which do not react with the new compounds, such as, for example, water, gelatine, lactose, starch, magnesium stearate, talc, vegetable oils, benzyl alcohol, rubber, polyalkylene glycols, white petroleum jelly, cholesterol or other known medicinal excipients. The pharmaceutical preparations can be, for example, in the form of tablets, dragées, capsules, suppositories, ointments or cream or in a liquid form, as solutions (for example as an elixir or syrup), suspensions or emulsions. They are optionally sterilised and/or contain auxiliaries, such as preservatives, stabilizers, wetting agents or emulsifiers, salts for regulating the osmotic pressure or buffers. They can also contain yet other therapeutically valuable materials. The preparations, which can also be used in veterinary medicine, are formulated according to customary methods.

The daily dose for a warm-blooded animal of aprrox. 75 kg body weight is about 20 to 120 mg administered orally. The examples which follow illustrate the invention without, however, restricting it.

EXAMPLE 1

10.46 g of 1-[2,3-epoxy-propoxy]-9,10-dihydro-9,10-ethano-anthracene and 12 ml of isopropylamine are dissolved in 220 ml of absolute alcohol and the solution is boiled for 20 hours under reflux. The reaction mixture is then evaporated to dryness and the residue is recrystallised from 75 ml of methylcyclohexane.

The base thus obtained melts at 102°–103° C. To prepare the hydrochloride, 7.95 g of this base are dissolved in 100 ml of isopropanol and 20 ml of 2.2 N alcoholic hydrochloric acid are added to the solution. The hydrochloride which has precipitated is filtered of, washed with isopropanol and dried at 70°–80° C and 12 mm Hg. The pure 1-[2-hydroxy-3-isopropylamino-propoxy]-9,10-dihydro-9,10-ethano-anthracene hydrochloride thus obtained melts at 236°–237° C.

1-[2,3-Epoxy-propoxy]-9,10-dihydro-9,10-ethano-anthracene, used as the starting material, can be prepared as follows:

20.0 g of 1-hydroxy-9,10-dihydro-9,10-ethano-anthracene, 25 ml of epichlorohydrin and 20 g of potassium hydroxide, in 150 ml of acetone are heated to the boil for 50 hours. After cooling, the inorganic salts are filtered off, the filtrate is evaporated, the evaporation residue is dissolved in 200 ml of methylene chloride and this solution is first extracted with three times 50 ml of 2 N sodium hydroxide solution and then additionally once with 50 ml of water.

The methylene chloride extract is dried with anhydrous magnesium sulphate and evaporated. The evaporation residue is first recrystallised from 90 ml of 95% strength alcohol and then again from 160 ml of 95% strength alcohol.

1-[2,3-Epoxy-propoxy]-9,10-dihydro-9,10-ethano-anthracene thus obtained, melts at 127°–130° C.

The requisite 1-hydroxy-9,10-dihydro-9,10-ethano-anthracene can be obtained by a 1,4-cycloaddition of 1-hydroxyanthracene to ethylene. After recrystallisation from methylcyclohexane, it has a melting point of 162°–163° C.

EXAMPLE 2

A solution of 20 g of methylamine in 150 ml of 95% strength alcohol is added all at once to a solution of 12.4 g of 1-[2,3epoxy-propoxy]-9,10-dihydro-9,10-ethano-anthracene. The reaction mixture is subsequently heated to the boil for 12 hours and is then evaporated to dryness. The evaporation residue is recrystallised three times from methylcyclohexane. The base thus obtained, which melts at 120°–129° C, is dissolved in 100 ml of isopropanol by warming, and 35 ml of 2.2 N alcoholic hydrochloric acid are added to the solution. The hydrochloride which precipitates is filtered off, washed with isopropanol and dried at 70°–80° C and 12 mm Hg. 1-[2-Hydroxy-3-methylamino-propoxy]-9,10-dihydro-9,10-ethano-anthracene hydrochloride, thus obtained, melts at 213° C.

EXAMPLE 3

Tablets containing 20 mg of active substance are prepared, in the following composition:

| | |
|---|---|
| 1-[2-Hydroxy-3-isopropylamino-propoxy]-9,10-dihydro-9,10-ethano-anthracene hydrochloride | 20 mg |
| Starch | 60 mg |
| Lactose | 50 mg |
| Colloidal silica | 5 mg |
| Talc | 9 mg |
| Magnesium stearate | 1 mg |
| | 145 mg |

Preparation

The 1-[2-hydroxy-3-isopropylamino-propoxy]-9,10-dihydro-9,10-ethano-anthracene hydrochloride is mixed with the lactose, a part of the wheat starch and with colloidal silica and the mixture is forced through a sieve, a powder mixture being obtained thereby. A further part of the wheat starch is worked into a paste with a 5-fold amount of water on a water bath and the powder mixture is kneaded with this paste until a slightly plastic mass has been produced.

The plastic mass is forced through a sieve of approx. 3 mm mesh width, and is dried, and the dry granules are again forced through a sieve. The remaining wheat starch, talc and magnesium stearate are then added and the resulting mixture is pressed to give tablets weighing 400 mg (and having a cross-shaped groove).

The daily dose is about 1 to 6 tablets in the case of a warm-blooded animal of about 75 kg body weight, it also being possible to administer the corresponding dose of active substance in a single tablet of appropriate composition.

EXAMPLE 4

The following mixture is used to prepare capsules:

| | |
|---|---|
| 1-[2-Hydroxy-3-isopropylamino-propoxy]-9,10-dihydro-9,10-ethano-anthracene hydrochloride | 2,500 g |
| Talc | 80 g |
| Colloidal silica | 20 g |

The active compound is intimately mixed with the talc and colloidal silica and the mixture is passed through a sieve (0.5 mm) and filled, in portions of 21 mg, into hard gelatine capsules of suitable size.

EXAMPLE 5

9.16 g of 1-[2,3-epoxy-propoxy]-9,10-dihydro-9,10-ethano-anthracene and 10 ml of tert.-butylamine are dissolved in 200 ml of absolute alcohol and the solution is boiled for 20 hours under reflux. The reaction mixture is then evaporated to dryness and the residue is recrystallised from 35 ml of methylcyclohexane.

The base thus obtained melts at 113°–115° C. To prepare the hydrochloride, 7.0 g of this base are dissolved in 40 ml of isopropanol and 25 ml of 2.0 N alcoholic hydrochloric acid are added to the solution. The hydrochloride which precipitates is filtered off, washed with isopropanol and dried at 70°–80° C and 12 mm Hg. The pure 1-[2-hydroxy-3-tert.-butylamino-propoxy]-9,10-dihydro-9,10-ethano-anthracene hydrochloride thus obtained melts at 230°–232° C.

EXAMPLE 6

13.9 g of 1-[2,3-epoxy-propoxy]-9,10-dihydro-9,10-ethano-anthracene and 60 ml of 33% strength dimethylamine solution (in absolute alcohol) are dissolved in 200 ml of absolute alcohol and the solution is boiled for 20 hours under reflux. The reaction mixture is then evaporated to dryness and the residue is recrystallised from 120 ml of cyclohexane. The base thus obtained melts at 101°–104° C. To prepare the hydrochloride, 6.6 g of this base are dissolved in 100 ml of isopropyl acetate and 30 ml of 2.2 N alcoholic hydrochloric acid are added to the solution. The hydrochloride which precipitates is filtered off, washed with isopropyl acetate and dried at 70°–80° C and 12 mm Hg. The pure 1-[2-hydroxy-3-dimthylamino-propoxy]-9,10-dihydro-9,10-ethano-anthracene hydrochloride thus obtained melts at 217°–220° C.

EXAMPLE 7

40.95 g of 2-[2,3-epoxy-propoxy]-9,10-dihydro-9,10-ethano-anthracene and 48 ml of isopropylamine are dissolved in 700 ml of absolute alcohol and the solution is boiled for 20 hours under reflux. The reaction mixture is then evaporated to dryness and the residue is recrystallised from 180 ml of toluene. 2-Hydroxy-3-isopropylamino-propoxy]-9,10-dihydro-9,10-ethano-anthracene thus obtained, melts at 126°–127° C.

2-[2,3-Epoxy-propoxy]-9,10-dihydro-9,10-ethano-anthracene, used as the starting material, can be prepared as follows:

30.0 g of 2-hydroxy-9,10-dihydro-9,10-ethanoanthracene, 153 ml of epichlorohydrin and 0.3 ml of piperidine are stirred for 20 hours at 100° C. After cooling, the reaction mixture is evaporated, the evaporation residue is dissolved in 450 ml of benzene and the solution is extracted by shaking with three times 150 ml of 2 N sodium hydroxide solution and then additionally with 150 ml of water. The benzene extract is dried with magnesium sulphate and evaporated. The viscous 2-[2,3-epoxy-propoxy]-9,10-dihydro-9,10-ethano-anthracene which remains can be employed without further purification.

The requisite 2-hydroxy-9,10-dihydro-9,10-ethano-anthracene can be obtained by a 1,4-cycloaddition of 2-hydroxy-anthracene to ethylene. After recrystallisation from toluene-methylcyclohexane, the product has a melting point of 147°–149° C.

What we claim is:

1. A compound of the formula III

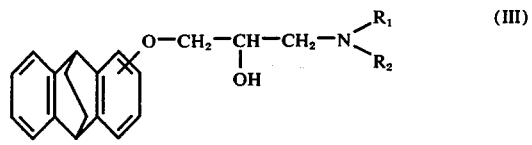

wherein $R_1$ represents hydrogen or lower alkyl, $R_2$ represents hydrogen or lower alkyl and the 3-amino-2-hydroxypropoxy side chain is in the 1- or 2-position of the anthracene skeleton, and the pharmaceutically acceptable salts thereof.

2. The compound according to claim 1, which is 1-[2-hydroxy-3-methylamino-propoxy]-9,10-dihydro-9,10-ethano-anthracene and the pharmaceutically acceptable salts thereof.

3. The compound according to claim 1, which is 1-[2-hydroxy-3-dimethylamino-propoxy]-9,10-dihydro-9,10-ethano-anthracene and the pharmaceutically acceptable salts thereof.

4. The compound according to claim 1, which is 1-[2-hydroxy-3-tert.-butylamino-propoxy]-9,10-dihydro-9,10-ethano-anthracene and the pharmaceutically acceptable salts thereof.

5. The compound according to claim 1, which is 2-[2-hydroxy-3-isopropylamino-propoxy]-9,10-dihydro-9,10-ethano-anthracene and the pharmaceutically acceptable salts thereof.

6. The compound according to claim 1 which is 1-[2-hydroxy-3-isopropylamino-propoxy]-9,10-dihydro-9,10-ethano-anthracene and the pharmaceutically acceptable salts thereof.

7. The compound of claim 6 which is the hydrochloride salt thereof.

* * * * *